(12) United States Patent
Morton

(10) Patent No.: US 10,386,532 B2
(45) Date of Patent: Aug. 20, 2019

(54) RADIATION SIGNAL PROCESSING SYSTEM

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 275 days.

(21) Appl. No.: 15/584,990

(22) Filed: May 2, 2017

(65) Prior Publication Data
US 2017/0329036 A1 Nov. 16, 2017

Related U.S. Application Data

(60) Provisional application No. 62/330,905, filed on May 3, 2016.

(51) Int. Cl.
*G01V 5/00* (2006.01)
*G01N 23/087* (2018.01)

(52) U.S. Cl.
CPC ........ *G01V 5/0041* (2013.01); *G01N 23/087* (2013.01); *G01N 2223/423* (2013.01)

(58) Field of Classification Search
CPC .... G01V 5/0041; G01N 23/04; G01N 23/087; G01N 2223/402; G01N 2223/403; G01N 2223/423; G06T 2207/10116
See application file for complete search history.

(56) References Cited

U.S. PATENT DOCUMENTS 7,453,987 B1 * 11/2008 Richardson .......... G01V 5/0041
378/57
2015/0104089 A1 * 4/2015 Litvin ................... G06T 11/006
382/131

* cited by examiner

*Primary Examiner* — Chih-Cheng Kao
(74) *Attorney, Agent, or Firm* — Novel IP

(57) ABSTRACT

A dual energy based X-ray scanning system has a linear detector array with high and low energy detectors. A signal processing method is employed that accounts for varying angles at which the transmitted X-rays impinge upon the detectors and also the varying order in which the transmitted X-rays pass through the high and low energy detectors. This yields both high resolution in the generated images and better penetration performance.

20 Claims, 11 Drawing Sheets

RADIATION SIGNAL PROCESSING SYSTEM

CROSS-REFERENCE TO RELATED APPLICATIONS

The present application relies upon U.S. Patent Provisional Application No. 62/330,905, entitled "Radiation Signal Processing System" and filed on May 3, 2016, for priority, which is also herein incorporated by reference in its entirety

FIELD

The present specification generally relates to the field of radiant energy imaging systems, and more specifically to an improved dual-energy based system for detecting concealed objects and identifying materials of interest.

BACKGROUND

Radiographic images are produced by the detection of radiation that is transmitted through or scattered from the object being inspected. The density, atomic number and the total amount of material that is present determine the extent of attenuation of the radiation and, therefore, the nature and type of radiographic image produced. By determining the average absorption of the X-ray or gamma ray photons as they travel along the various X-ray paths, it is possible to derive information about the characteristics of the material through which they pass. The intensity of scattered X-rays is related to the atomic number (Z) of the material scattering the X-rays. In general, for atomic numbers less than 25, the intensity of X-ray backscatter, or X-ray reflectance, decreases with increasing atomic number. On the other hand, materials with high atomic number (Z>70) are characterized by high attenuation of the low and high end of the X-ray spectrum. Therefore, the X-ray images are primarily modulated by variation in the atomic number various materials present inside an object (such as within cargo).

As the final image is modulated in accordance with the atomic numbers of various materials present inside an object, it is common for X-ray imaging systems to produce images with dark areas. Although these dark areas might indicate the presence of threat materials, they yield little information about the exact nature of threat. In addition, the radiographs produced by conventional X-ray systems are often difficult to interpret because in these radiographs, the objects are superimposed which may confound the image. Therefore, a trained operator must study and interpret each image to render an opinion on whether or not a target of interest, such as a threat, is present. Operator fatigue and distraction can compromise detection performance when a large number of such radiographs are to be interpreted, such as at high traffic transit points and ports. Even with automated systems, it becomes difficult to comply with the implied requirement to keep the number of false alarms low, when the system is operated at high throughputs.

One method of obtaining more useful information and clarity from X-ray imaging is using dual energy systems to measure the effective atomic numbers of materials in containers or luggage. Here, the X-ray beam is separated into two broad categories: low energy X-ray beam and high energy X-ray beam. Often this is achieved by passing the X-ray beam through a first thin X-ray detector that responds preferentially to low-energy X-radiation. This filtered beam is then passed to a second detector, which responds to the remaining X-ray beam, which is weighted towards the higher energy part of the spectrum. Effective atomic number is then determined by taking the difference between the high energy and low energy signals. This method is particularly effective for X-ray energy beams in the range of 60 kV to 450 kV where the rapid change in linear attenuation coefficient of the object under inspection gives good contrast between the low and high-energy spectral regions.

Some of the challenges in processing high and low energy signals in a dual energy system, which, in turn, affect the accuracy of the calculated result, include varying angles at which the transmitted X-rays impinge upon the detectors and also the varying order in which the transmitted X-rays pass through the high and low energy detectors.

Accordingly, there is a need for improved method and system for signal processing in dual energy imaging systems, that addresses the challenges faced by conventional methods of signal processing and provides not only for high resolution in the generated images but also for better penetration performance.

SUMMARY

In embodiments, the present specification discloses a signal processing method for a dual energy based X-ray scanning system comprising an X-ray source configured to generate high energy X-rays and low energy X-rays and a linear detector array having at least a high energy X-ray detector configured to detect said high energy X-rays and produce high energy pixel data and a low energy X-ray detector configured to detect said low energy X-rays and produce low energy pixel data, the method comprising: using said linear detector array, generating said high energy pixel data and low energy pixel data; using a processor in data communication with said linear detector array, sampling the high energy pixel data and low energy pixel data onto a shape to create sampled high energy pixel data and sampled low energy pixel data respectively in a form of a locus of points; using said processor, calculating a plurality of equivalent detector thicknesses based upon the sampled high energy pixel data and sampled low energy pixel data; using said processor, determining a value of an effective Z based upon said plurality of equivalent detector thicknesses; using said processor, determining a value of intensity for said sampled high energy pixel data and low energy pixel data; using said processor, generating an image based upon the effective Z and the intensity; displaying said image on a display.

Optionally, sampling the high energy pixel data and low energy pixel data onto a shape comprises interpolating the high energy pixel data and low energy pixel data as equidistant points on a predetermined arc.

Optionally, determining the value of the effective Z further comprises using sampled high energy pixel data and sampled low energy pixel data.

Optionally, determining the value of the effective Z comprises accessing a look up table to retrieve data relating the effective Z to a function of said plurality of equivalent detector thicknesses. Optionally, said function is determined by measuring transmission through absorbers with known characteristics placed in path of said X-ray source configured to generate the high energy X-rays and the low energy X-rays. Still optionally, the high energy X-rays and the low energy X-rays are passed through said absorbers by placing the absorbers on a motorized conveyance adjacent to said X-ray source.

Optionally, said absorbers comprise a plurality of different materials positioned in a step-wise arrangement. Optionally, said plurality of different materials comprises plastic, aluminum, and steel.

Optionally, said absorbers comprise a plurality of different materials wherein each material of said plurality of different materials has a different length and is positioned atop another material of said plurality of different materials to create a step-wise arrangement.

Optionally, determining the value of intensity of the sampled high energy pixel data and low energy pixel data comprises using the sampled high energy pixel data, the sampled low energy pixel data, and a predetermined variable acquired from a look up table.

Optionally, the predetermined variable is determined from a curve that weights an amount of high energy required in order to compensate for a decreasing low energy pixel.

In some embodiments, the present specification discloses a dual energy X-ray scanning system comprising: an X-ray source configured to generate high energy X-rays and low energy X-rays; a linear detector array having a plurality of high energy X-ray detectors configured to detect said high energy X-rays and produce high energy pixel data and a plurality of low energy X-ray detectors configured to detect said low energy X-rays and produce low energy pixel data; a controller comprising a processor in data communication with a non-transient memory, wherein said processor is configured to: receive said high energy pixel data and low energy pixel data; sample the high energy pixel data and low energy pixel data onto a shape to create sampled high energy pixel data and sampled low energy pixel data respectively in a form of a locus of points; calculate a plurality of equivalent detector thicknesses based upon the sampled high energy pixel data and sampled low energy pixel data; determine a value of an effective Z based upon said plurality of equivalent detector thicknesses; determine a value of intensity for said sampled high energy pixel data and low energy pixel data; and generate an image based upon the effective Z and the intensity; and a display in data communication with said controller and configured to receive said image and display said image.

Optionally, sampling the high energy pixel data and low energy pixel data onto a shape comprises interpolating the high energy pixel data and low energy pixel data as equidistant points on a predetermined arc.

Optionally, determining the value of the effective Z further comprises using sampled high energy pixel data and sampled low energy pixel data.

Optionally, determining the value of the effective Z comprises accessing a look up table to retrieve data relating the effective Z to a function of said plurality of equivalent detector thicknesses.

Optionally, said function is determined by measuring transmission through absorbers with known characteristics placed in path of said X-ray source configured to generate the high energy X-rays and the low energy X-rays.

Optionally, said high energy X-rays and the low energy X-rays are passed through said absorbers by placing the absorbers on a motorized conveyance adjacent to said X-ray source and wherein said absorbers comprise a plurality of different materials positioned in a step-wise arrangement.

Optionally, said plurality of different materials comprise plastic, aluminum, and steel and wherein each material of said plurality of different materials has a different length and is positioned atop another material of said plurality of different materials to create a step-wise arrangement.

Optionally, determining the value of intensity of the sampled high energy pixel data and low energy pixel data comprises using the sampled high energy pixel data, the sampled low energy pixel data, and a predetermined variable acquired from a look up table.

Optionally, the predetermined variable is determined from a curve that weights an amount of high energy required in order to compensate for a decreasing low energy pixel.

In an embodiment, the present specification describes a signal processing method for a dual energy based X-ray scanning system comprising a linear detector array comprising at least a high energy X-ray detector and a low energy X-ray detector, the detectors detecting X-rays to produce detected image pixels, the method comprising: re-sampling the HE (High Energy) and LE (Low Energy) detected pixel data into an alternative locus of points; calculating the LE and HE equivalent detector thicknesses for each spatially re-sampled pixel from the original pixel data; determining a value of the effective Z for each re-sampled pixel; determining a value of intensity for each re-sampled pixel pair; and presenting a displayed image by using the re-sampled pixel values of effective Z and intensity.

Optionally, the step of re-sampling the detected pixels into an alternative locus of points comprises interpolating the detected pixels as equidistant points on a predetermined arc.

Optionally, the step of determining a value of the effective Z comprises using at least: high and low energy values of the detected pixels and thickness values of the high and low energy detectors of the linear detector array.

Optionally, the step of determining a value of the effective Z comprises using a function of the thickness of high energy detectors and low energy detectors determined by using a look up table. Optionally, the function of the thickness of high energy detectors and low energy detectors is obtained by using absorbers with known characteristics in path of X-rays emitted in the X-ray scanning system.

Optionally, the emitted X-ray beam is passed through absorbers of a plurality of materials having known characteristics by placing the materials on a motorized conveyance adjacent to an X-ray source of the X-ray scanning system.

Optionally, the step of determining a value of intensity of the detected pixels comprises using at least: high and low energy values of the detected pixels and a predetermined variable obtained from a look up table. Optionally, the predetermined variable is obtained from a curve that best weights the amount of high energy required in order to compensate for a decreasing low energy pixel.

Optionally, the detected image is a generically uniform image which can be presented on any display terminal coupled with the X-ray scanning system.

In an embodiment, the present specification describes a dual energy based X-ray scanning system comprising a linear detector array comprising at least a high energy X-ray detector and a low energy X-ray detector, the detectors detecting X-rays to produce detected image pixels, the detected image pixels being processed to obtain a detected image, the processing comprising: re-sampling the HE (High Energy) and LE (Low Energy) detected pixel data into an alternative locus of points; calculating the LE and HE equivalent detector thicknesses for each spatially re-sampled pixel from the original pixel data; determining a value of the effective Z for each re-sampled pixel; determining a value of intensity for each re-sampled pixel pair; and presenting a displayed image by using the re-sampled pixel values of effective Z and intensity.

Optionally, the step of re-sampling the detected pixels into an alternative locus of points comprises interpolating the detected pixels as equidistant points on a predetermined arc.

Optionally, the step of determining a value of the effective Z comprises using at least: high and low energy values of the detected pixels and thickness values of the high and low energy detectors of the linear detector array. Optionally, the step of determining a value of the effective Z comprises using a function of the thickness of high energy detectors and low energy detectors determined by using a look up table.

Optionally, the detected image is a generically uniform image which can be presented on any display terminal coupled with the X-ray scanning system.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

Figure 1:
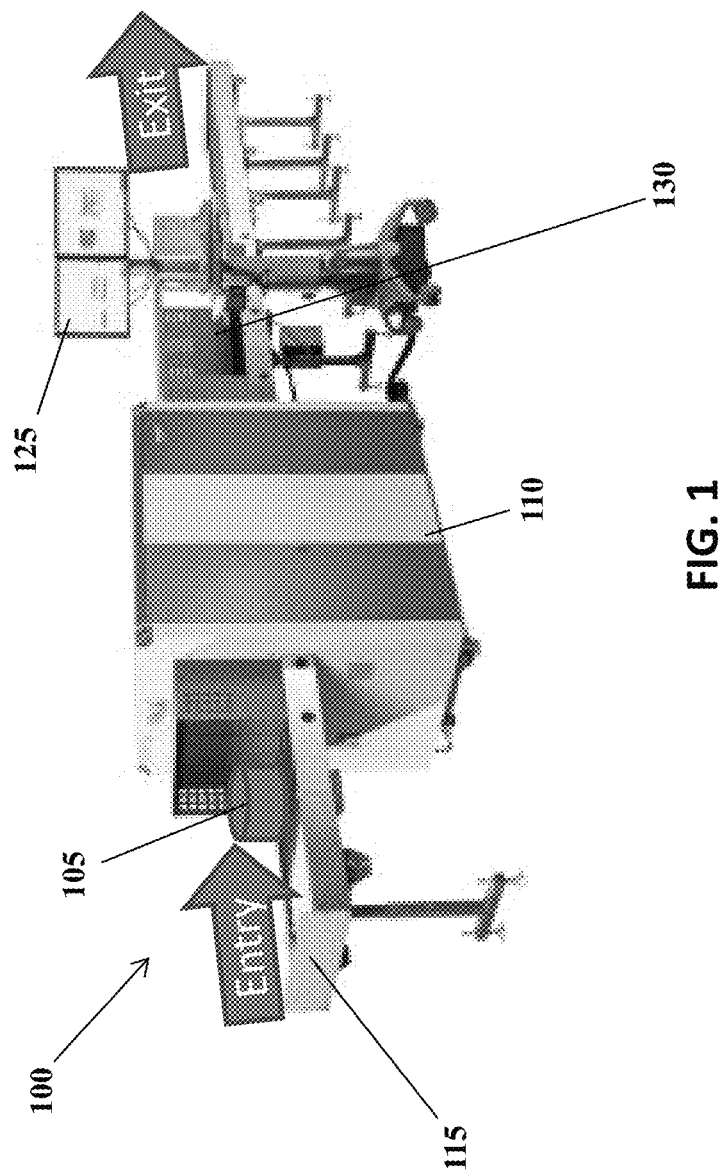
FIG. 1 is an overview of an exemplary dual-energy X-ray based imaging system.

The present specification describes improved low and high energy linear radiation detector arrays for a dual energy imaging system, wherein the two sets of detectors (corresponding to high and low energy) of the linear detector array have different degrees of segmentation. Segmentation refers to the division of the detector into smaller discrete sections. When a detector has more segmentation, it provides finer pixelation, thereby improving its spatial resolution and can be used to specifically identify the precise position of an impinging X-ray. In comparison, a thicker or lesser level of segmentation in a detector provides for more volume for the impending X-ray to hit or be absorbed/be detected. In an embodiment of the present specification, a high-energy detector has a coarser pixelation (thicker segmentation), thereby improving its penetration performance. In an embodiment, a low energy detector is provided with a finer segmentation. It may be appreciated that higher resolution for a low energy detector also provides an enhanced wire resolution or the greater ability to see small wires, while a lower resolution for a high-energy detector yields improved penetration performance. In various embodiments, the present specification provides a linear detector array providing both low and high-energy characteristics.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

It should further be appreciated that all the methods described herein are executed on a processor and are embodied in programmatic instructions stored in a non-transient memory. The processor is in data communication with one or more components of the disclosed X-ray system, including the X-ray scanner, detector array, and/or display monitors. The processor may comprise any number of chips, system on chip modules, motherboards, integrated hardware platforms, or distributed hardware platforms.

FIG. 1 provides an overview of an exemplary dual-energy X-ray based imaging system. In this example, the imaging system is used for baggage inspection, commonly employed at airports and other transit points. Referring to FIG. 1, in operation of the X-ray inspection system 100, objects 105 such as baggage, are translated on a conveyor 115 through a baggage scanning enclosure 110. The enclosure 110 comprises an X-ray source and a plurality of detector elements. The X-ray source irradiates the conveyed object 105 with penetrating radiation while the detector elements collect the radiation transmitted through the object 105. The levels of collected radiation are processed using a processing system, such as a computer to generate and if required, store, scan images of the conveyed objects 105. In certain machine configurations, images may be stored. The duration for which the images are stored is based on the requirement. The generated images are presented onto a viewing device, such as a monitor 125, for an operator to review/examine the images. In certain modes of operation, the images are sent to a remote operator. Subsequently, if the operator desires to physically inspect contents of a scanned object, based on the operator's review of the corresponding images, the operator can do so by stopping the conveyor 115 at an appropriate time to enable accessing the scanned object through an access area 130. An exemplary implementation of the X-ray based imaging system 100 is the Rapiscan 620DV system, which is a dual-view, multi-energy system, and is commercially available from Rapiscan Systems, Inc.

In embodiments, low energy x-ray signals have an energy ranging from 20 keV to a maximum tube energy. In embodiments, low energy x-ray signals have an energy ranging from 50 keV to a maximum tube energy. In an embodiment, the maximum tube energy is 160 keV. The fraction or ratio of low energy signal compared to high energy signal is greater in the low energy detector that for the high energy detector.

In various embodiments, the present specification provides a linear detector array. Conventionally, a detector array is segmented into short sections wherein each section is about 100 mm long. Within the array, each section is angled such that it is perpendicular to the X-ray beam at a point of incidence. However, such a detector array is difficult to manufacture. The present specification addresses this issue by providing a detector array having linearly placed high and low energy detectors.

Figure 2:
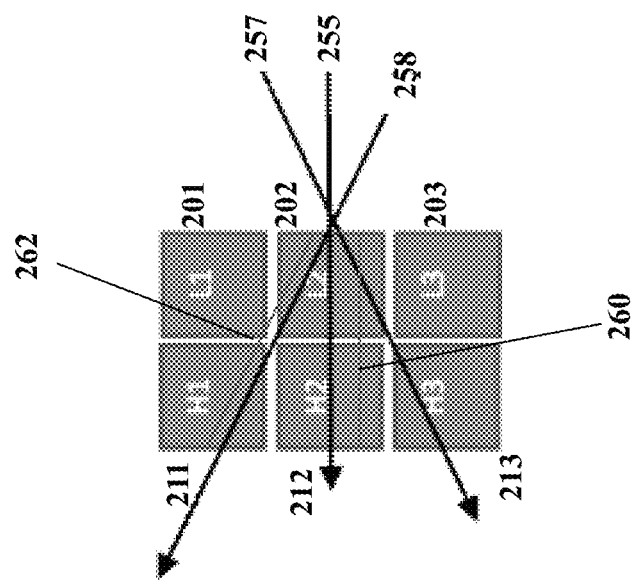
FIG. 2 illustrates a linear detector array and the angles of various X-rays transmitted through the detector array, according to an embodiment of the present specification.

One of the problems encountered in processing high and low energy signals in a dual energy system by using the linear detector array such as the one provided by the present specification, is that as the angle of the transmitted X-ray changes, the area of detector it passes through also changes, which may lead to cross talk. This is illustrated in FIG. 2. Referring to FIG. 2, L1 201, L2 202 and L3 203 are low energy detectors placed adjacent to high-energy detectors H1 211, H2 212 and H3 213. X-rays 255, 257 and 258 impinge upon the high and low energy detectors at various angles. Thus, ray 257 passes through the detectors L2 202 and H3 213, ray 255 passes through L2 202 and H2 212, ray 258 passes through L2 202 and H1 211. It may be noted from the figure that the X-ray 255 impinges perfectly perpendicularly upon the detectors. This X-ray passes through a certain width of the two adjoining detectors, which may be called X 260. However, rays 257 and 258 impinge upon the detectors at an angle, and therefore they pass through a width 262 of two adjoining detectors which is greater than X 260, since the distance travelled by ray 257 through L2 202 and H3 213 is greater than the distance travelled by ray 255 through L2 202 and H2 212. Thus, dual energy signals need to be adjusted for this variation while processing.

Further, as the angle at which an X-ray impinges upon the detectors changes, the alignment between the high and low energy detectors also changes. Therefore the angle variation not only means that different X-rays pass through different thicknesses of detectors, but also that an X-ray may pass through a first detector and a second detector that is not immediately behind the first detector, but adjacent to it. Therefore, this means that the high energy X-ray impinges on a high-energy detector in one position and the associated low energy component of the same X-ray beam impinges on a detector in a different position, thereby creating confusion over where the X-ray actually came from. Consequently, the processing of pixels is required to be adjusted for this variation as well. The present specification provides a method to effectively deal with the aforementioned signal processing issues.

Figure 3:
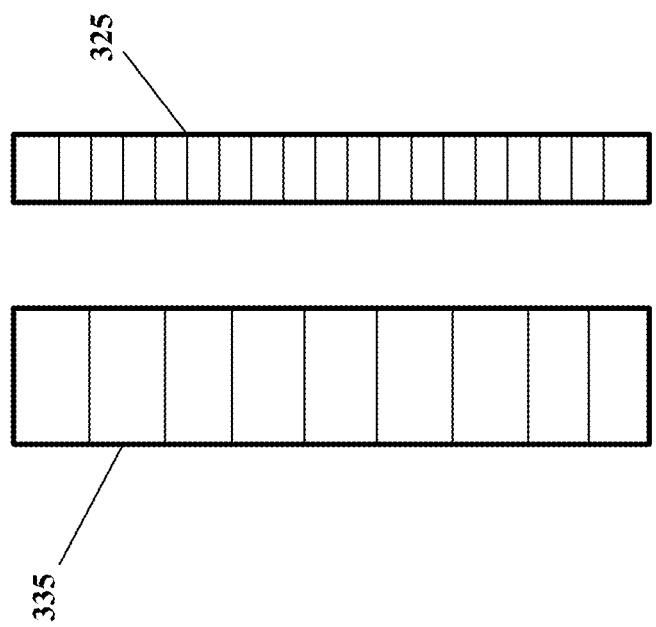
FIG. 3 is a schematic diagram illustrating a linear detector array comprising high and low energy detectors, according to an embodiment of the present specification.

In an embodiment, the method is carried out by the processing system of the X-ray imaging system (as described with reference to FIG. 1), which generates images of the objects scanned using X-radiation. FIG. 3 is a schematic diagram illustrating a linear detector array comprising both high and low energy detectors, in accordance with an embodiment of the present specification. Referring to FIG. 3, a series of high energy (HE) detectors 335 are placed adjacent to a series of low energy (LE) detectors 325, thereby forming a dual energy linear detector array. In an embodiment, the high energy detectors 335 are thickly segmented low resolution detectors, designed for improved penetration performance, while the low energy (LE) detectors 325 are thinly segmented high resolution detectors, designed for improved wire resolution (ability to see small wires). Stated differently, each HE detector has a greater thickness than its adjacent LE detector. In another embodiment, every HE detector has a greater thickness than every LE detector in the detector array. In another embodiment, each HE detector has a thickness that, relative to its adjacent LE detector, is anywhere from 1% to 300% thicker, and every numerical increment within that range.

Figure 4:
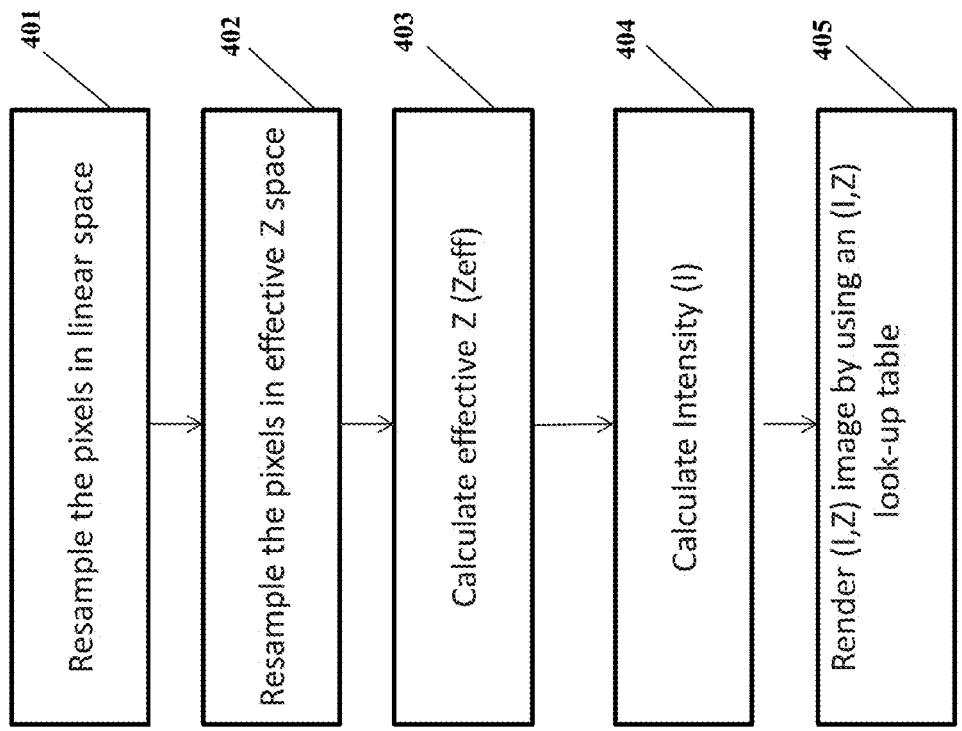
FIG. 4 is a flowchart illustrating a signal processing method, according to an embodiment of the present specification.
Figure 5:
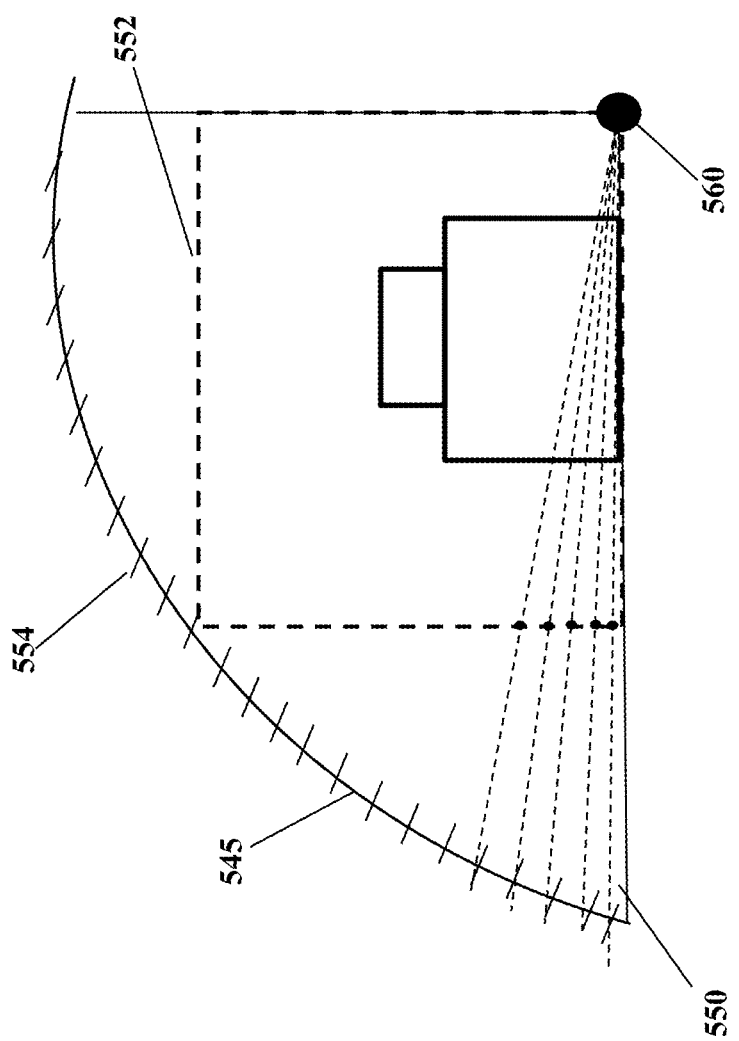
FIG. 5 illustrates a graphical representation of a method of sampling detected pixels, in accordance with an embodiment of the present specification.

FIG. 4 is a flowchart illustrating the method of processing signals, according to an embodiment. Referring to FIG. 4, at step 401 the detected pixels are sampled in linear space. In an embodiment, the sampling is performed by interpolating the detected pixels as equidistant points on an imaginary arc. X-rays passing through the high and low energy detectors generate corresponding high energy/low energy signals, where each detector signal may represent a pixel. FIG. 5 illustrates a graphical representation of a method of sampling detected pixels, in accordance with an embodiment of the present specification. As shown in FIG. 5, these signals are interpolated such that they map on to an imaginary arc 545 with equidistant points. In various embodiments, the signals may be interpolated onto any virtual shape, to generate an alternative locus of points, which may also allow operators to expand or compress the image in order to adjust the aspect ratio of the image. Further, in embodiments, a different locus of points may be used for each type of view geometry.

The arc 545 shown in FIG. 5 implies that dense pixel numbers in the corner 550 and sparse numbers towards the edges 552 are projected into an equally spaced arc. In embodiments, the physical detector elements 325, 335 (shown in FIG. 3) are positioned along the edge of a scanning tunnel, hence denser detector signal(s) (pixels) are observed near the corners 550 of the detector array further away from a radiation source 560, as represented in FIG. 5.

This is the first step in the processing method, and involves re-sampling pixels in linear space. Therefore, values from one or more low energy detectors are re-sampled into one equivalent scaled low energy pixel while one or more high energy detector values are re-sampled into one equivalent high energy pixel. The result is two new sets of data (one data set corresponding to low energy radiation and the other data set corresponding to high energy radiation) which are the equivalent of pixel arrays that are arranged in a perpendicular fashion, where such re-sampled pixel 554 is located along the new locus, such as an arc.

Each low and high energy pixel in the re-scaled high and low energy data sets corresponds to a subtly different front sensor thickness and rear sensor thickness depending on the angle of incidence of the X-ray beam at that point in the array. For example, with a beam of perpendicular incidence (e.g. trajectory 255 shown in FIG. 2), the thickness of the low and high energy detector material traversed by the X-ray beam is equal to the actual thickness of a single low energy detector and a single high energy detector. In contrast, for a beam of oblique incidence (e.g. trajectory 258 shown in FIG. 2), the thickness of low and high energy detector material traversed by the X-ray beam will be greater the actual thickness of a single low energy detector and a single high energy detector. Therefore, it is necessary, for the calculation of effective atomic number (Z-effective) of materials in the X-ray beam path between the X-ray source and the detector array, to measure or calculate a set of weighting functions, one dual weighting function per high and low energy re-scaled pixel, which would compensate for the variation in thickness of detector material traversed by beam corresponding to each rescaled dual-energy pixel.

Referring back to FIG. 4, at step 402, the sampled pixels are calibrated for equivalent thickness of detector material at both the high energy and low energy re-sampled pixels prior to calculation of the effective atomic number (Zeff) of the materials in the path between the X-ray source and the detector array. Zeff is the aggregate atomic number that is representative of all the materials in the X-ray beam between the X-ray source and the detectors.

At step 403, Zeff is calculated by using the following equation:

$$Zeff = (Hi_i - Lo_i)/(Hi_i + Lo_i) + w_i(thi_i/tlo_i) \quad (1)$$

Where $Hi_i$ refers to High energy at pixel i;
$Lo_i$ refers to Low energy at pixel i;
$thi_i$ refers to thickness of the high energy detector at pixel i;
$tlo_i$ refers to thickness of the low energy detector at pixel i; and
$w_i$ refers to a function of the thickness of high energy detector to low energy detector.

In an embodiment, $w_i$ is calculated by using a look up table and determined based on a process discussed later in the specification. In an embodiment, contents of the look-up-table are generated using computational means, such as but not limited to, through a Monte Carlo model of the X-ray imaging system, or by experimental measurements of the X-ray beam properties. It will be appreciated by one of ordinary skill in the art that alternative methods may be used to calculate Z effective including but not limited to using logarithmic values of $Hi_i$ and $Lo_i$, using alternate weighting factors and using non-linear combinations of $Hi_i$ and $Lo_i$.

At the next step 404, intensity ($I_i$) is calculated on a pixel basis, using the following equation:

$$I_i = (Lo_i + alpha(Lo_i)Hi_i)/(1 + alpha(Lo_i)) \quad (2)$$

where alpha is a variable from a look up table;
$Lo_i$ is low object attenuation; and
$H_i$ is high object attenuation.

Figure 6:
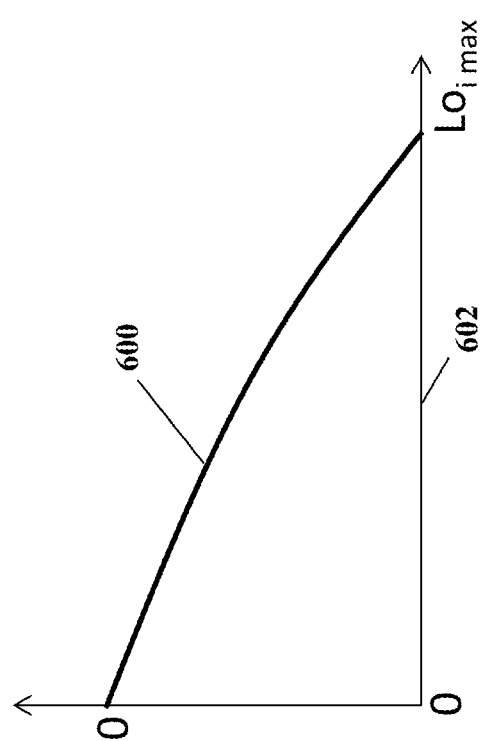
FIG. 6 illustrates an exemplary alpha curve, according to an embodiment of the present specification.

In an embodiment, alpha is set to zero for high values of $Lo_i$ (low object attenuation) and is increased to 1 for small values of $Lo_i$ (nearing high object attenuation). Between these two points, alpha is defined as a continuous monotonically increasing curve of a pre-defined shape. Typically, the same alpha curve should be used for all pixels in the image. FIG. 6 illustrates an exemplary alpha curve 600 corresponding to values of $Lo_i$ ranging from 0 to maximum shown on x-axis 602. As can be seen in FIG. 6 alpha is represented as an arbitrary curve 600 with a value of zero at a maximum value of $Lo_i$ and the value of alpha increases to 1 at a minimum (or zero) value of $Lo_i$. In embodiments, alpha is determined as a curve that best weights the amount of high energy required in order to compensate for a decreasing low energy signal in order to maximize displayed spatial resolution while simultaneously providing highest penetration performance.

Referring back to FIG. 4, in order to render the final image on the inspection screen, at step 405 each pixel in the image is colored according to both its Intensity and its Zeff. This is typically achieved using a look-up-table.

Figure 7:
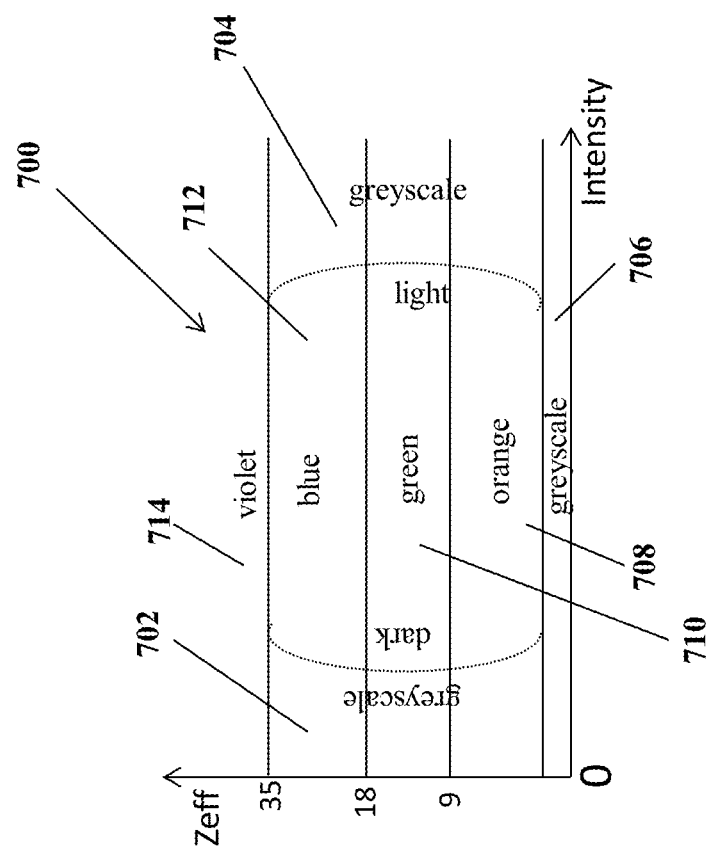
FIG. 7 illustrates an exemplary look-up table that may be used for rendering a radiation image on a screen, according to an embodiment of the present specification.

FIG. 7 illustrates an exemplary look-up table 700 that may be used for rendering a radiation image on a screen, in accordance with an embodiment of the present specification. In an embodiment, for very thin material thicknesses (e.g. less than 1% beam attenuation), the radiation image is generally colored in grayscale. For very high object attenuation (e.g. greater than 1 in 10,000), the image is also colored in grayscale and between the two grayscale regions, the image is colored according to material type. Look-up table 700 illustrates a plot of material intensities against their respective Zeff values, along with corresponding colors to be applied to the radiation image. As shown, pixels of materials falling in the regions 702, 704 and 706 are represented in grayscale, organic materials having a low Zeff value 708 are represented in orange, inorganic materials having intermediate Zeff values 710 are represented in green, materials having a high Zeff value 712 are represented in blue and materials having very high Zeff values 714 are represented in violet. In other embodiments, any suitable color scheme may be selected to represent materials having different Zeff values in a radiation image in as many color bands as required in the particular application.

Figure 8:
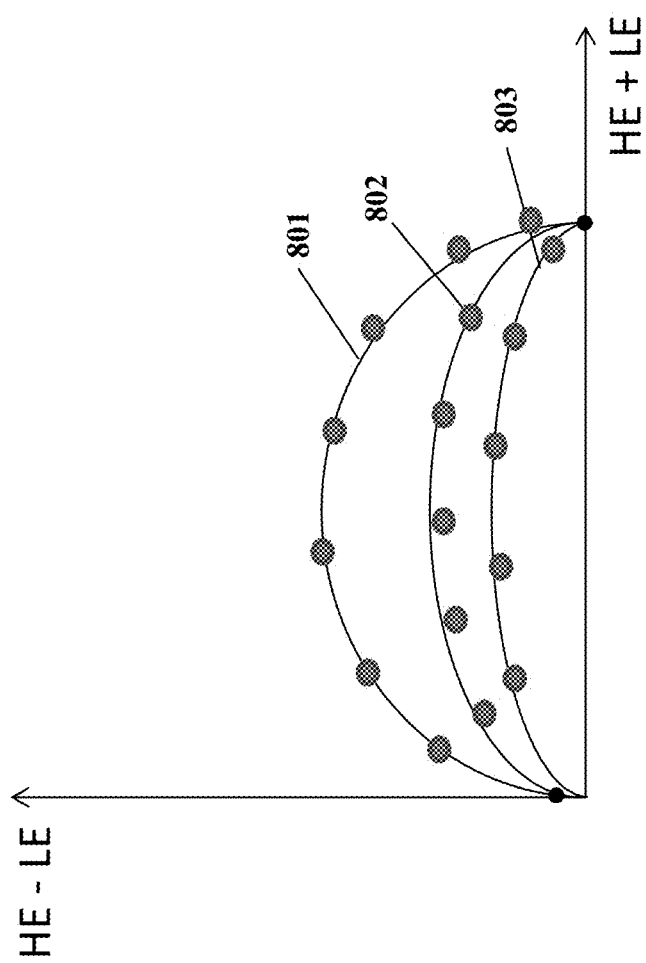
FIG. 8 illustrates a graph where HE−LE versus HE+LE curves are plotted corresponding to three exemplary materials, according to an embodiment of the present specification.

In an embodiment of the present specification, the function of the thickness of high energy detector to low energy detector (w from equation (1)), which is required for calculating the effective atomic number (Zeff) of the materials in the path between the X-ray source and the detector array, is calculated by putting an absorber of known thickness into the X-ray beam. One of ordinary skill in the art would appreciate that known absorber materials—such as nylon, lead, steel, and aluminum have known characteristics such as density, thickness, effective atomic number (Zeff) and linear attenuation coefficient. Since 'w' is a function of thickness and composition of both the high energy and low energy detectors, it may be measured experimentally. To calculate 'w', and hence determine Zeff, it is conventional to plot experimental data corresponding to each material in the form of a graph of HE−LE versus HE+LE, where HE refers to high energy and LE refers to low energy. FIG. 8 illustrates a graph where HE−LE versus HE+LE curves are plotted corresponding to three exemplary materials including steel 801, aluminum 802 and plastic 803. Once these curves have been plotted, they can be used to determine the Zeff of any arbitrary material by interpolating the curves corresponding to materials with known Zeff in the vertical axis for given HE+LE value.

Figure 9:
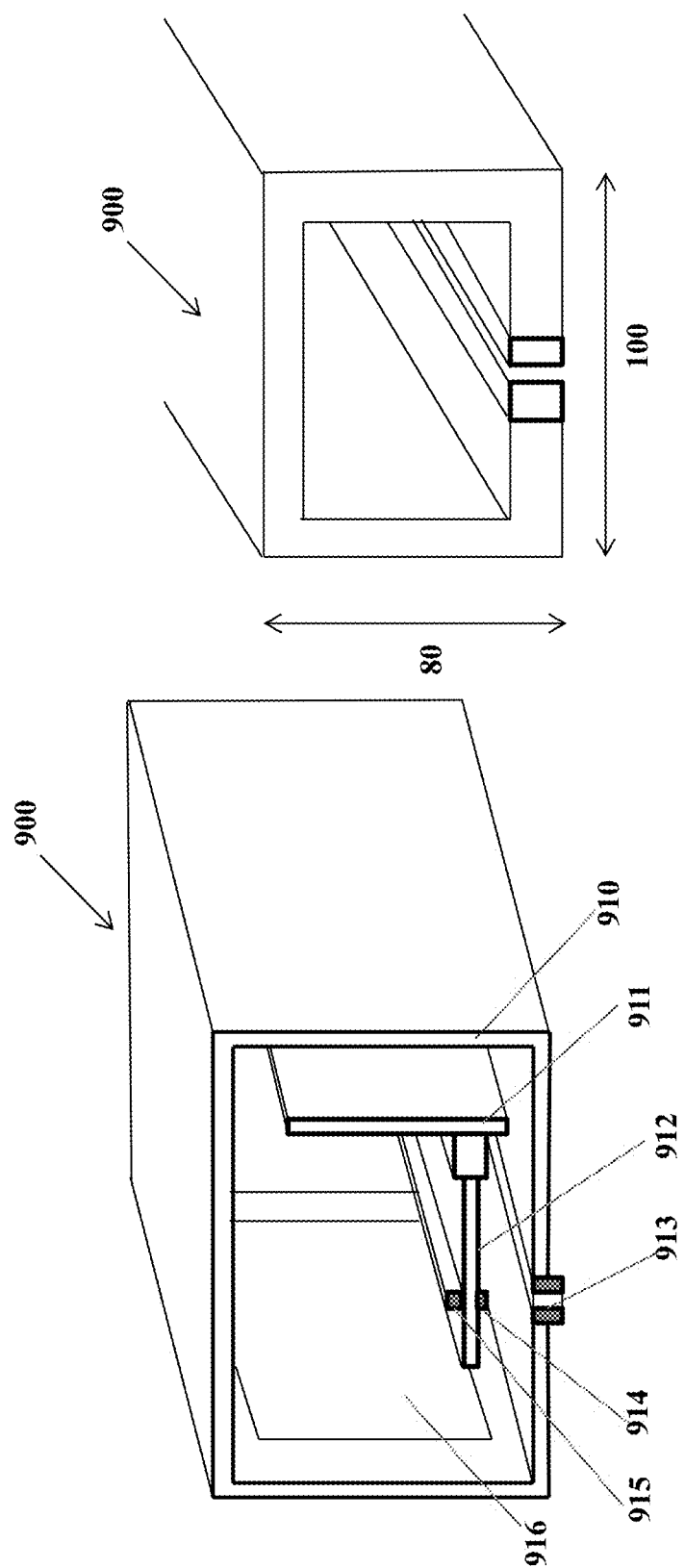
FIG. 9 illustrates an exemplary detector assembly, according to an embodiment of the present specification.

In FIG. 9, a representative detector assembly 600 is shown in accordance with an embodiment of the present specification. The detector assembly 600 comprises an outer enclosure 910 which does not allow light to pass through, a data acquisition circuit board 911, a detector circuit board 912 containing a linear detector array comprising low energy detectors 914 and high energy detectors 915 which detect X-rays passing through a collimator aperture 913. A service access port 916 is provided on a wall of the outer enclosure 910 to allow maintenance of the detectors 914, 6915 and data acquisition circuit board 911. In an embodiment, the detector assembly 900 extends around two or three sides of the scanning tunnel in order to form a fan-beam X-ray image of the object under inspection. In an embodiment, as shown in FIG. 9 the dimensions of a front face of detector assembly 900 are 100 mm by 80 mm.

In a preferred embodiment, radiation shielding is placed adjacent to and as an integral part of the X-ray detector in order to minimize stray and scattered radiation from interacting with the data acquisition electronics and to minimize the overall radiation footprint of the machine.

Figure 10A:
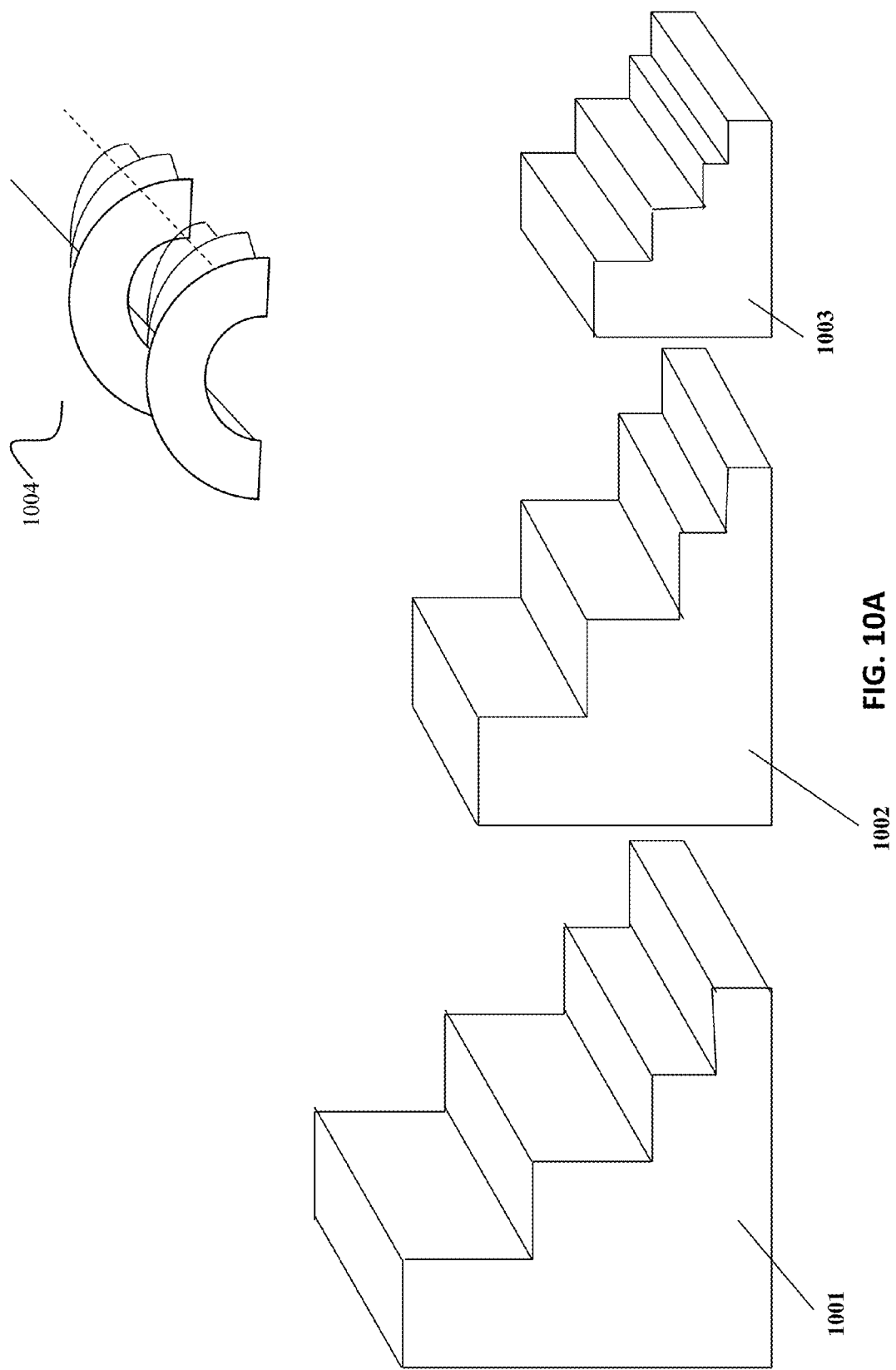
FIG. 10A illustrates absorbers that may be placed in a beam path, according to an embodiment of the present specification.
Figure 10B:
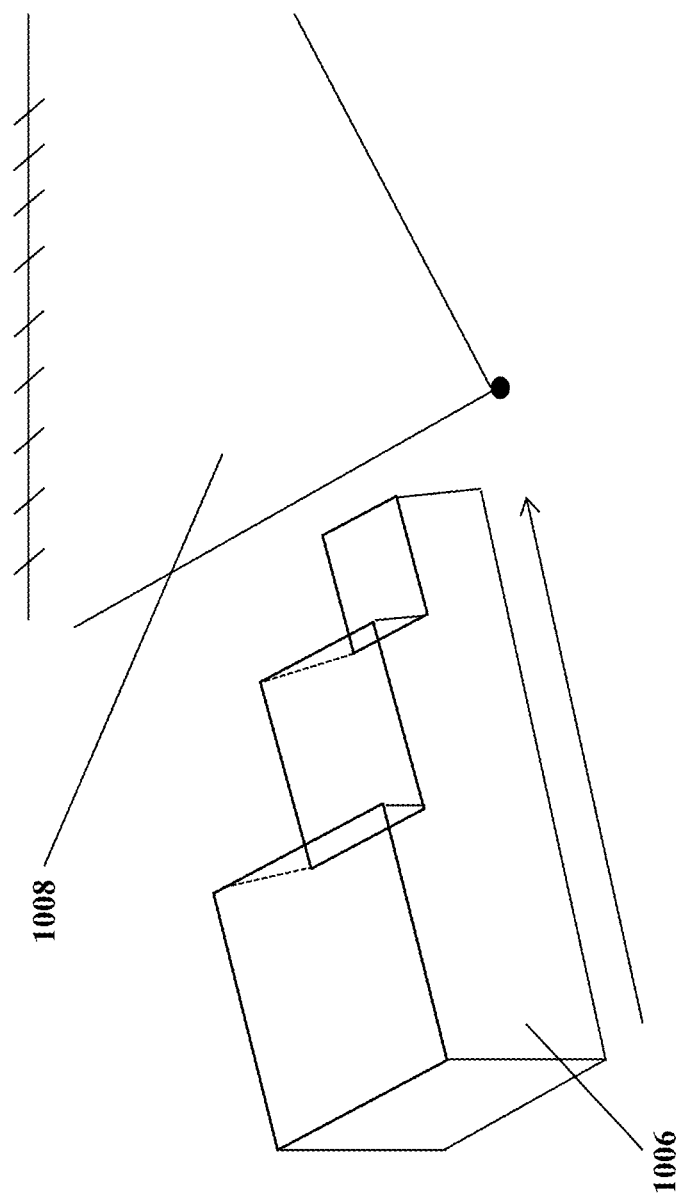
FIG. 10B illustrates absorbers placed in the beam path, according to one embodiment of the present specification.

In an embodiment, the X-ray beam is passed through absorbers of different materials by placing the absorbers on a motorized conveyance adjacent to an X-ray source. FIGS. 10A and 10B illustrate placement of absorbers in the beam path. Referring to FIG. 10A, in an embodiment, three absorbers made up of plastic 1001, aluminum 1002 and steel 1003 are placed in a step wedge arrangement in the beam path. Once scanned, the data from these step wedge absorbers is used to create a Zeff chart, such as the one shown in FIG. 8 in order to calibrate the imaging system for quantitative imaging. In an alternative embodiment, the absorbers may be arranged as cylindrical step wedges 1004 of known materials such as steel, aluminum and nylon. As shown in FIG. 10B, these absorber step wedges 1006 may be incorporated into the imaging system design itself, such that they wrap around the X-ray tube of the system and may be inserted and removed from the X-ray beam 708 as part of a routine calibration procedure.

It may be appreciated that the present signal processing approach of re-sampling in the spatial domain, calculating Zeff, and calculating intensity to yield a re-sampled image results in a Zeff (Z) versus Intensity (I) image. This Z versus I image creates a generically uniform data set which can be presented on any display terminal. Conventionally, display terminals require machine-specific information in order to adjust images for machine-specific data. With the present signal processing approach however, when the detector arrays output calibrated Z and I images, the machine specific variations are automatically accounted for. Thus, the display terminal only needs to have one look up table corresponding to Z vs. I, in order to identify a material of interest. One of ordinary skill in the art would appreciate that the Z vs. I look up table is universal and provides the same result regardless of the type of machine being used. That is, a specific point on the Z vs. I table shall correspond to the same material regardless of the machine being used.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A signal processing method for a dual energy based X-ray scanning system comprising an X-ray source configured to generate high energy X-rays and low energy X-rays and a linear detector array having at least a high energy X-ray detector configured to detect said high energy X-rays and produce high energy pixel data and a low energy X-ray detector configured to detect said low energy X-rays and produce low energy pixel data, the method comprising:
using said linear detector array, generating said high energy pixel data and low energy pixel data;
using a processor in data communication with said linear detector array, sampling the high energy pixel data and low energy pixel data onto a shape to create sampled high energy pixel data and sampled low energy pixel data respectively in a form of a locus of points;
using said processor, calculating a plurality of equivalent detector thicknesses based upon the sampled high energy pixel data and sampled low energy pixel data;
using said processor, determining a value of an effective Z based upon said plurality of equivalent detector thicknesses;
using said processor, determining a value of intensity for said sampled high energy pixel data and low energy pixel data;
using said processor, generating an image based upon the effective Z and the intensity; and
displaying said image on a display.

2. The signal processing method of claim 1 wherein sampling the high energy pixel data and low energy pixel data onto a shape comprises interpolating the high energy pixel data and low energy pixel data as equidistant points on a predetermined arc.

3. The signal processing method of claim 1 wherein determining the value of the effective Z further comprises using sampled high energy pixel data and sampled low energy pixel data.

4. The signal processing method of claim 1 wherein determining the value of the effective Z comprises accessing a look up table to retrieve data relating the effective Z to a function of said plurality of equivalent detector thicknesses.

5. The signal processing method of claim 4 wherein said function is determined by measuring transmission through absorbers with known characteristics placed in a path of said X-ray source configured to generate the high energy X-rays and the low energy X-rays.

6. The signal processing method of claim 5 wherein the high energy X-rays and the low energy X-rays are passed through said absorbers by placing the absorbers on a motorized conveyance adjacent to said X-ray source.

7. The signal processing method of claim 5 wherein said absorbers comprise a plurality of different materials positioned in a step-wise arrangement.

8. The signal processing method of claim 7 wherein said plurality of different materials comprise plastic, aluminum, and steel.

9. The signal processing method of claim 5 wherein said absorbers comprise a plurality of different materials, wherein each material of said plurality of different materials has a different length and is positioned atop another material of said plurality of different materials to create a step-wise arrangement.

10. The signal processing method of claim 1 wherein determining the value of intensity of the sampled high energy pixel data and low energy pixel data comprises using the sampled high energy pixel data, the sampled low energy pixel data, and a predetermined variable acquired from a look up table.

11. The signal processing method of claim 10 wherein the predetermined variable is determined from a curve that weights an amount of high energy required in order to compensate for a decreasing low energy pixel.

12. A dual energy X-ray scanning system comprising:
an X-ray source configured to generate high energy X-rays and low energy X-rays;
a linear detector array having a plurality of high energy X-ray detectors configured to detect said high energy X-rays and produce high energy pixel data and a plurality of low energy X-ray detectors configured to detect said low energy X-rays and produce low energy pixel data;

a controller comprising a processor in data communication with a non-transient memory, wherein said processor is configured to:
  receive said high energy pixel data and low energy pixel data;
  sample the high energy pixel data and low energy pixel data onto a shape to create sampled high energy pixel data and sampled low energy pixel data respectively in a form of a locus of points;
  calculate a plurality of equivalent detector thicknesses based upon the sampled high energy pixel data and sampled low energy pixel data;
  determine a value of an effective Z based upon said plurality of equivalent detector thicknesses;
  determine a value of intensity for said sampled high energy pixel data and low energy pixel data; and
  generate an image based upon the effective Z and the intensity; and
a display in data communication with said controller and configured to receive said image and display said image.

13. The dual energy X-ray scanning system of claim 12 wherein sampling the high energy pixel data and low energy pixel data onto a shape comprises interpolating the high energy pixel data and low energy pixel data as equidistant points on a predetermined arc.

14. The dual energy X-ray scanning system of claim 12 wherein determining the value of the effective Z further comprises using sampled high energy pixel data and sampled low energy pixel data.

15. The dual energy X-ray scanning system of claim 12 wherein determining the value of the effective Z comprises accessing a look up table to retrieve data relating the effective Z to a function of said plurality of equivalent detector thicknesses.

16. The dual energy X-ray scanning system of claim 15 wherein said function is determined by measuring transmission through absorbers with known characteristics placed in a path of said X-ray source configured to generate the high energy X-rays and the low energy X-rays.

17. The dual energy X-ray scanning system of claim 15 wherein said high energy X-rays and the low energy X-rays are passed through absorbers by placing the absorbers on a motorized conveyance adjacent to said X-ray source and wherein said absorbers comprise a plurality of different materials positioned in a step-wise arrangement.

18. The dual energy X-ray scanning system of claim 17 wherein said plurality of different materials comprise plastic, aluminum, and steel and wherein each material of said plurality of different materials has a different length and is positioned atop another material of said plurality of different materials to create a step-wise arrangement.

19. The dual energy X-ray scanning system of claim 12 wherein determining the value of intensity of the sampled high energy pixel data and low energy pixel data comprises using the sampled high energy pixel data, the sampled low energy pixel data, and a predetermined variable acquired from a look up table.

20. The dual energy X-ray scanning system of claim 19 wherein the predetermined variable is determined from a curve that weights an amount of high energy required in order to compensate for a decreasing low energy pixel.

* * * * *